United States Patent [19]

Traber et al.

[11] Patent Number: 4,777,177

[45] Date of Patent: Oct. 11, 1988

[54] PESTICIDAL THIOXANTHEN-9-YLIDENEPIPERIDINES

[75] Inventors: Walter Traber, Reinach; Hanspeter Fischer, Bottmingen, both of Switzerland

[73] Assignee: Ciba-Geigy Corporation, Ardsley, N.Y.

[21] Appl. No.: 786,380

[22] Filed: Oct. 10, 1985

[30] Foreign Application Priority Data

Oct. 19, 1984 [CH] Switzerland .................. 5010/84
Oct. 19, 1984 [CH] Switzerland .................. 5011/84
Sep. 5, 1985 [CH] Switzerland .................. 3830/85

[51] Int. Cl.$^4$ ............................. A01N 43/18
[52] U.S. Cl. ..................... 514/324; 546/202
[58] Field of Search .................. 546/202; 514/324

[56] References Cited

U.S. PATENT DOCUMENTS

| | | | |
|---|---|---|---|
| 3,275,640 | 9/1966 | Engelhardt et al. | 546/202 |
| 3,361,753 | 1/1968 | Krumkalns | 260/294.8 |
| 3,408,355 | 10/1968 | Renz et al. | 546/202 |
| 3,470,188 | 9/1969 | Kaiser et al. | 546/202 |
| 4,021,561 | 5/1977 | Remy et al. | 424/267 |
| 4,076,714 | 2/1978 | Anderson et al. | 424/267 |
| 4,086,350 | 4/1978 | Zirkle | 514/324 X |
| 4,235,916 | 11/1980 | Bogeso | 514/324 |
| 4,356,184 | 10/1982 | Deason et al. | 514/324 |

FOREIGN PATENT DOCUMENTS

| | | | |
|---|---|---|---|
| 268765 | 11/1963 | Australia | 546/202 |
| 005607 | 11/1979 | European Pat. Off. | |
| 047226 | 3/1982 | European Pat. Off. | |
| 2290202 | 6/1976 | France | |
| 2256392 | 5/1973 | Fed. Rep. of Germany | 546/202 |
| 518974 | 3/1972 | Switzerland | 546/202 |
| 942876 | 11/1963 | United Kingdom | |
| 1495890 | 12/1977 | United Kingdom | 546/202 |

OTHER PUBLICATIONS

Journal of Chemical Chemistry, vol. 17, No. 1 pp. 57-61 (1974); Kaiser et al.

*Primary Examiner*—Joseph Paul Brust
*Attorney, Agent, or Firm*—Kevin T. Mansfield; Edward McC. Roberts

[57] ABSTRACT

The invention relates to the use in pest control of thioxanthen-9-ylidenepiperidines of formula I

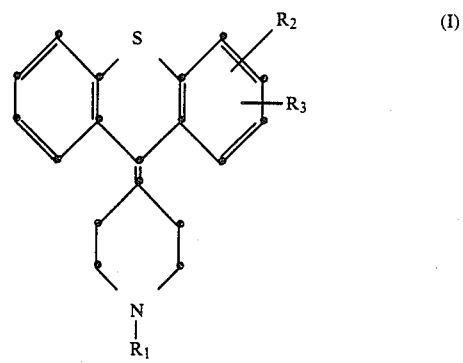

wherein
$R_1$ is hydrogen, $C_1$-$C_4$alkyl, $C_3$-$C_5$alkenyl, $C_3$-$C_5$alkynyl, cyano or —$COR_4$,
$R_2$ and $R_3$ independently of each other are hydrogen, halogen, $C_1$-$C_4$alkyl, $C_1$-$C_4$alkoxy, $C_1$-$C_4$haloalkyl or nitro,
$R_4$ is

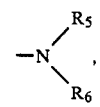

$C_1$-$C_4$alkyl, $C_1$-$C_4$alkoxy-$C_1$-$C_4$alkyl, $C_1$-$C_4$haloalkyl, $C_3$-$C_6$cycloalkyl,

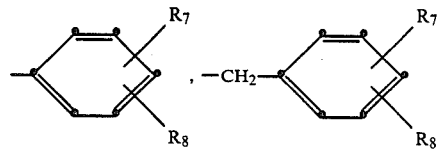

or $C_1$-$C_4$alkoxycarbonyl,
$R_5$ and $R_6$ independently of each other are hydrogen, $C_1$-$C_4$alkyl or $C_1$-$C_4$alkoxy and
$R_7$ and $R_8$ independently of each other are hydrogen, halogen, $C_1$-$C_4$alkyl, $C_1$-$C_4$alkoxy or nitro, and of the salts thereof and to compositions containing compounds of formula I as active ingredient.

29 Claims, No Drawings

PESTICIDAL THIOXANTHEN-9-YLIDENEPIPERIDINES

The present invention relates to the use of thioxanthen-9-ylidenepiperidines and the salts thereof in pest control, as well as to compositions which contain as active ingredient such thioxanthen-9-ylidenepiperidines and to the preparation of such compounds. The thioxanthen-9-ylidenepiperidines to be employed in accordance with this invention are of the formula

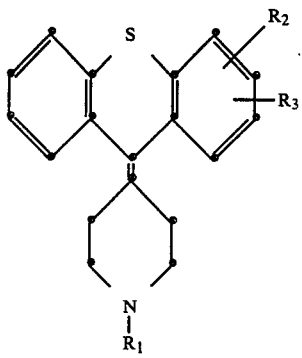

(I)

wherein
$R_1$ is hydrogen, $C_1$–$C_4$alkyl, $C_3$–$C_5$alkenyl, $C_3$–$C_5$alkynyl, cyano or —$COR_4$,
$R_2$ and $R_3$ independently of each other are hydrogen, halogen, $C_1$–$C_4$alkyl, $C_1$–$C_4$alkoxy, $C_1$–$C_4$haloalkyl or nitro,
$R_4$ is

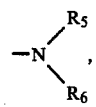

$C_1$–$C_4$alkyl, $C_1$–$C_4$alkoxy-$C_1$–$C_4$alkyl, $C_1$–$C_4$haloalkyl, $C_3$–$C_6$cycloalkyl,

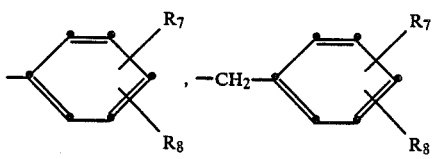

or $C_1$–$C_4$alkoxycarbonyl,
$R_5$ and $R_6$ independently of each other are hydrogen, $C_1$–$C_4$alkyl or $C_1$–$C_4$alkoxy and
$R_7$ and $R_8$ independently of each other are hydrogen, halogen, $C_1$–$C_4$alkyl, $C_1$–$C_4$alkoxy or nitro.

Suitable inorganic acids for the formation of salts of compounds of formula I are e.g. HCl, H$_2$SO$_4$, HBr and H$_3$PO$_4$ and suitable organic acids are e.g. saturated and unsaturated monocarboxylic, dicarboxylic and tricarboxylic acids such as formic acid, acetic acid, oxalic acid, phthalic acid, succinic acid and citric acid.

Halogen will be understood as meaning fluorine, chlorine, bromine or iodine, with chlorine or fluorine being preferred.

Alkyl, alkoxy, alkenyl, alkynyl and haloalkyl groups as defined for $R_1$, $R_2$ and $R_3$ may be straight chain or branched. Examples of such groups include: methyl, methoxy, trifluoromethyl, ethyl, ethoxy, propyl, isopropyl, n-butyl, isobutyl, sec-butyl, tert-butyl, —CH$_2$—CH=CH$_2$ and CH$_2$—C≡CH.

Cycloalkyl groups as defined for $R_4$ are for example cyclopropyl and cyclohexyl.

The invention also relates to the novel compounds of the formula

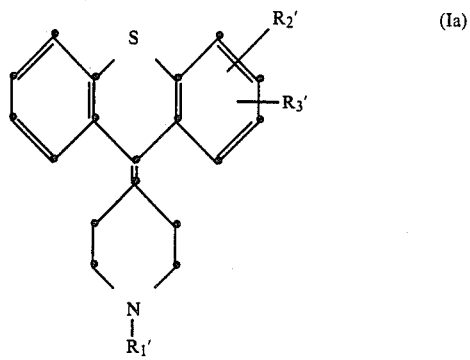

(Ia)

wherein
$R_1'$ is hydrogen,
$R_2'$ is bromine, $C_2$–$C_4$alkyl, $C_2$–$C_4$alkoxy, —CHF$_2$ or nitro and
$R_3'$ is hydrogen, halogen, $C_1$–$C_4$alkyl, $C_1$–$C_4$alkoxy, $C_1$–$C_4$haloalkyl or nitro or
$R_1'$ is ethyl, propyl, isopropyl, n-butyl, isobutyl, sec-butyl or tert-butyl and
$R_2'$ and $R_3'$ independently of each other are hydrogen, fluorine, bromine, $C_1$–$C_4$alkyl, $C_1$–$C_4$alkoxy, —CHF$_2$ or nitro or
$R_1'$ is propyl or isopropyl,
$R_2'$ is chlorine and
$R_3'$ is hydrogen, halogen, $C_1$–$C_4$alkyl, $C_1$–$C_4$alkoxy, $C_1$–$C_4$haloalkyl or nitro or
$R_1'$ is cyano and
$R_2'$ and $R_3'$ are hydrogen or
$R_1'$ is —$COR_4'$ or —CH$_2$—C≡CH,
$R_2'$ and $R_3'$ independently of each other are hydrogen, halogen, $C_1$–$C_4$alkyl, $C_1$–$C_4$alkoxy, $C_1$–$C_4$haloalkyl or nitro,
$R_4'$ is

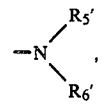

$C_1$–$C_4$alkyl, $C_1$–$C_4$haloalkyl, $C_3$–$C_6$cycloalkyl,

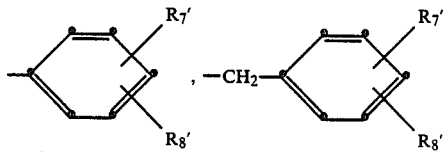

or carbonyloxy-$C_1$–$C_4$alkyl,
$R_5'$ and $R_6'$ independently of each other are hydrogen, $C_1$–$C_4$alkyl or $C_1$–$C_4$alkoxy and
$R_7'$ and $R_8'$ independently of each other are hydrogen, halogen, $C_1$–$C_4$alkyl, $C_1$–$C_4$alkoxy or nitro or
$R_1'$ is —CH$_2$—CH=CH$_2$ and
$R_2'$ and $R_3'$ independently of each other are hydrogen, halogen, $C_1$–$C_4$alkyl, $C_1$–$C_4$alkoxy or nitro, and to the salts thereof.

The compounds of formulae I and Ia are prepared by methods known per se, e.g. as follows:

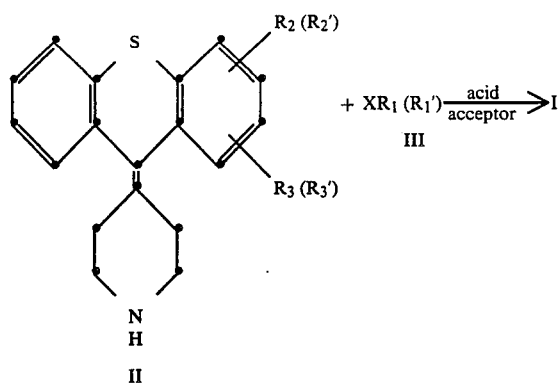

In formulae II and III, $R_1$, $R_2$ and $R_3$ are as defined for formula I and $R_1'$, $R_2'$ and $R_3'$ are as defined for formula Ia.

X in formula III is a halogen atom, preferably chlorine. Suitable acid acceptors are e.g. tertiary amines such as trialkylamines and pyridine, and also hydrides, hydroxides, oxides, carbonates and bicarbonates of alkali metals and alkaline earth metals, as well as alkali metal alcoholates such as potassium tert-butylate and sodium methylate.

The process is carried out at a temperature in the range from $-10°$ to $150°$ C., usually in the range from $20°$ to $80°$ C., under normal pressure and preferably in an inert solvent or diluent. Suitable solvents or diluents are e.g. ethers and ethereal compounds such as diethyl ether, dipropyl ether, dioxane, dimethoxyethane and tetrahydrofuran; amides such as N,N-dialkylated carboxamides; aliphatic, aromatic and halogenated hydrocarbons, in particular benzene, toluene, xylenes, chloroform and chlorobenzene; nitriles such as acetonitrile; dimethyl sulfoxide; and ketones such as acetone and methyl ethyl ketone.

The compounds of formulae II and III are known and can be prepared by methods analogous to known ones.

It is known from French patent specification No. 2 290 202 that compounds of formula I exhibit pharmaceutical activity.

Surprisingly, it has been found that compounds of formulae I and Ia are also suitable for controlling pests of animals and plants as well as for controlling phytophathogenic fungi.

The compounds of formulae I and Ia are effective against the phytopathogenic fungi belonging to the following classes: Ascomycetes (e.g. Erysiphaceae, Fusarium, Helminthosphorium); Basidiomycetes such as Puccinia, Rhizoctonia, Tilletia, Hemileia; Fungi imperfecti (e.g. Cercospora, Botrytis, Septoria); Phycomycetes such as Phytophthora. In addition, the compounds of formulae I and Ia have a systemic action. The compounds of formulae I and Ia are advantageously used as dressing agents for protecting seeds and stored goods (fruit, tubers, grains) and plant cuttings against fungus infections as well as against phytopathogenic fungi which occur in the soil.

The compounds of formulae I and Ia are particularly suitable for controlling insects, for example of the orders Lepidoptera, Coleoptera, Homoptera, Heteroptera, Diptera, Thysanoptera, Orthoptera, Anoplura, Siphonaptera, Mallophaga, Thysanura, Isoptera, Psocoptera and Hymenoptera and mites and ticks of the order Acarina.

The compounds of formulae I and Ia are especially suitable for controlling plant-destructive insects, in particular plant-destructive feeding insects, in ornamentals and crops of useful plants, in particular in cotton and rice crops (e.g. *Spodoptera littoralis, Heliothis virescens, Chilo suppressalis* and *Laodelphax*) and in vegetable and fruit crops (e.g. *Leptinotarsa decemlineata, Myzus persicae, Laspeyresia pomonella* and *Adoxophyes reticulana*), and for controlling soil insects (e.g. *Aulacophora femoralis, Chortophila brassicae, Diabrotica balteata, Pachnoda savignyi* and *Scotia ypsilon*).

The compounds of formulae I and Ia are also very effective against flies, e.g. Musca domestica and mosquito larvae. They influence the behaviour of the insects, in particular the feeding behaviour and the flight orientation.

The acaricidal and/or insecticidal action can be substantially broadened and adapted to prevailing circumstances by addition of other insecticides and/or acaricides. Examples of suitable additives include: organophosphorus compounds, nitrophenols and derivatives thereof, formamidines, ureas, pyrethroids, carbamates, and chlorinated hydrocarbons.

Compounds of formulae I and Ia are also combined with particular advantage with substances which exert a synergistic or potentiating effect e.g. on the pheromone perception. Examples of such compounds include: piperonyl butoxide, propynyl ether, propynyl oximes, propynyl carbamates and propynyl phosphates, 2-(3,4-methylenedioxyphenoxy)-3,6,9-trioxaundecane (Sesamex or Sesoxane), S,S,S,-tributylphosphorotrithioates, 1,2-methylenedioxy-4-(2-(octylsulfinyl)propyl)-benzene.

The compounds of formulae I and Ia are used in unmodified form, or preferably together with the adjuvants conventionally employed in the art of formulation, and are therefore formulated in known manner to emulsifiable concentrates, directly sprayable or dilutable solutions, dilute emulsions, wettable powders, soluble powders, dusts, granulates, and also encapsulations in e.g. polymer substances. As with the nature of the compositions, the methods of application such as spraying, atomising, dusting, scattering or pouring, are chosen in accordance with the intended objectives and the prevailing circumstances.

The formulations, i.e. the compositions or preparations containing the compound (active ingredient) of formula I or Ia and, where appropriate, a solid or liquid adjuvant, are prepared in known manner, e.g. by homogeneously mixing and/or grinding the active ingredients with extenders, e.g. solvents, solid carriers, and in some cases surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol, ethylene glycol monomethyl or monoethyl ether, ethyl acetate, propyl myristate or propyl palmitate, ketones such as cyclohexanone, strongly polar solvents such as N-methyl-2-pyrrolidone, dimethyl sulfoxide or dimethyl formamide, as well as vegetable oils or epoxidised vegetable oils such as epoxidised coconut oil or soybean oil; silicone oils or water.

The solid carriers used e.g. for dusts and dispersible powders are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable non-sorbent carriers are materials such as calcite or sand. In addition, a great number of pregranulated materials of inorganic or organic nature can be used, e.g. especially dolomite or pulverised plant residues.

Depending on the nature of the compound of formula I or Ia to be formulated, suitable surface-active compounds are nonionic, cationic and/or anionic surfactants having good emulsifying, dispersing and wetting properties. The term "surfactants" will also be understood as comprising mixtures of surfactants.

Suitable anionic surfactants can be both water-soluble soaps and water-soluble synthetic surface-active compounds.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained, e.g. from coconut oil or tallow oil. Further suitable surfactants are also the fatty acid methyltaurin salts.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammonium salts and contain a $C_8$–$C_{22}$alkyl radical which also includes the alkyl moiety of acyl radicals, e.g. the sodium or calcium salt of lignosulfonic acid, of dodecylsulfate, or of a mixture of fatty alcohol sulfates obtained from natural fatty acids. These compounds also comprise the salts of sulfuric acid esters and sulfonic acids of fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnaphthalenesulfonic acid, or of a naphthalenesulfonic acid/formaldehyde condensation product. Also suitable are corresponding phosphates, e.g. salts of the phosphoric acid ester of an adduct of p-nonylphenol with 4 to 14 moles of ethylene oxide.

Non-ionic surfactants are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediaminopolypropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, castor oil thioxilate, polypropylene/polyethylene oxide adducts, tributylphenoxypolyethoxyethanol, polyethylene glycol and octylphenoxypolyethoxyethanol. Fatty acid esters of polyoxyethylene sorbitan, e.g. polyoxyethylene sorbitan trioleate, are also suitable non-ionic surfactants.

Cationic surfactants are preferably quaternary ammonium salts which contain, as N-substituent, at least one $C_8$–$C_{22}$alkyl radical and, as further substituents, unsubstituted or halogenated lower alkyl, benzyl of hydroxy-lower alkyl radicals. The salts are preferably in the form of halides, methylsulfates or ethylsulfates, e.g. stearyl-trimethylammonium chloride or benzyldi(2-chloroethyl)ethylammonium bromide.

The surfactants customarily employed in the art of formulation are described e.g. in "McCutcheon's Detergents and Emulsifiers Annual", MC Publishing Corp., Ringwood, N.J., 1982, and Dr. Helmut Stache: "Tensid Taschenbuch" (Handbook of Surfactants), Carl Hanser Verlag, Munich/Vienna, 1981.

The pesticidal compositions usually contain 0.1 to 99%, preferably 0.1 to 95%, of a compound of formula I or Ia, 1 to 99.9% of a solid or liquid adjuvant, and 0 to 25%, preferably 0.1 to 25%, of a surfactant.

Whereas commercial produets are preferably formulated as concentrates, the end user will normally employ dilute formulations.

The compositions may also contain further ingredients, such as stabilisers, antifoams, viscosity regulators, binders, tackifiers as well as fertilisers or other active ingredients for obtaining special effects.

EXAMPLE 1

Preparation of Compound 1 of the Formula

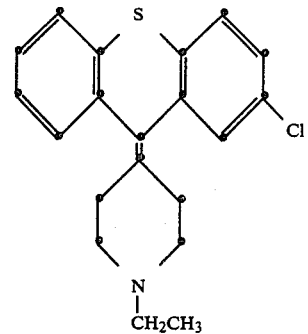

A solution of 0.66 g of sodium hydride in 30 ml of tetrahydrofuran is added dropwise for 20 minutes at 21° C. to a solution of 6.3 g of 4-(2-chlorothioxanthen-9-ylidene)piperidine in 70 ml of tetrahydrofuran. The reaction solution is boiled under reflux for 22 hours and then left to stand for 48 hours at room temperature. Then 3.12 g of ethyl iodide are added all at once. The reaction solution is boiled under reflux for a further 24 hours and then poured into 400 g of ice water and the product is extracted with methylene chloride. The organic phase is separated, dried over magnesium sulfate and concentrated.

Chromatography of the crude product over silica gel (elution with a 95:5 mixture of toluene and ethyl acetate) affords the title compound with a melting point of 55°–58° C.

The following compounds are also prepared in analogous manner:

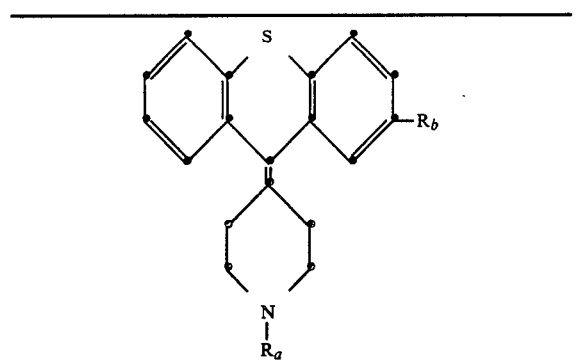

| Comp. | $R_a$ | $R_b$ | Melting point |
|---|---|---|---|
| 2 | CH₃ | H | 120–121° C. |
| 3 | CH₃ | Cl | 107–109° C. |
| 4 | CN | H | 194–196° C. |
| 5 | H | H | 143–145° C. |
| 6 | CN | Cl | 155–157° C. |
| 7 | H | Cl | 142–143° C. |
| 8 | C₃H₇(n) | H | 156–157° C. |
| 9 | C₂H₅ | H | 105–107° C. |
| 10 | C₃H₇(i) | Cl | 60° C. |
| 11 | C₃H₇(n) | Cl | 68–72° C. |
| 12 | —C(O)—(2,5-dimethylphenyl) | H | 94–97° C. |
| 13 | —CH₂—CH=CH₂ | H | 131–133° C. |
| 14 | —CH₂—CH=CH₂ | Cl | 120–122° C. |
| 15 | —CH₂—C≡CH | H | 53–56° C. |
| 16 | —CH₂—C≡CH | Cl | 57–59° C. |
| 17 | —C(O)—CH(CH₂CH₂) (cyclopropyl) | H | 190–192° C. |
| 18 | —C(O)CH₂Cl | H | 126–128° C. |
| 19 | —C(O)NHCH₃ | H | 229–231° C. |
| 20 | —C(O)—N(CH₃)₂ | H | 127–129° C. |
| 21 | —C(O)—CH₂—(4-chlorophenyl) | Cl | 119–121° C. |
| 22 | —C(O)—N(OCH₃)(CH₃) | Cl | 152–155° C. |
| 23 | —C(O)—CH₂OCH₃ | Cl | 76–79° C. |

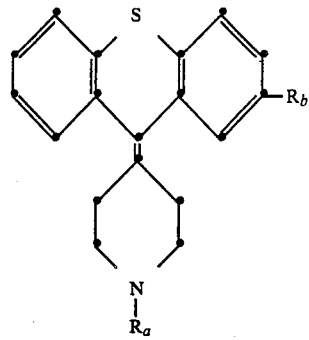

| Comp. | $R_a$ | $R_b$ | Melting point |
|---|---|---|---|
| 24 | —C(O)—C(O)—OC₂H₅ | H | 118–120° C. |
| 25 | —C(O)—CH(CH₃)—C₂H₅ | Cl | 86–88° C. |
| 26 | —C(O)NH₂ | H | 241–243° C. |
| 27 | CH₃ | CF₃ | 100–101° C. |

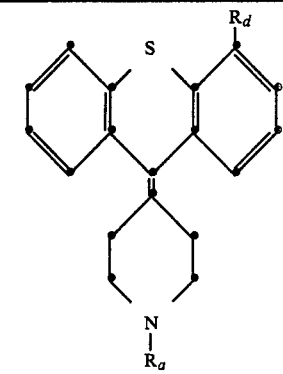

| Comp. | $R_a$ | $R_c$ | Melting point |
|---|---|---|---|
| 28 | CH₃ | Cl | 134–145° C. |
| 29 | CH₃ | CH₃ | 60° C. |

| Comp. | $R_a$ | $R_d$ | Melting point |
|---|---|---|---|
| 30 | CH₃ | Cl | 102–104° C. |

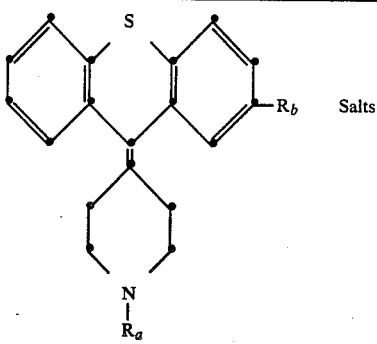

| Comp. | $R_a$ | $R_b$ | | Melting point |
|---|---|---|---|---|
| 31 | CH$_3$ | H | •HCl | 153–155° C. |
| 32 | CH$_3$ | CH$_3$ | •HBr | 189–181° C. |
| 33 | CH$_3$ | H | •CF$_3$COOH | 205° C. |

EXAMPLE 2

Formulation Examples for Active Ingredients of Formulae I and Ia According to Preparatory Example 1 (Throughout, Percentages are by Weight)

| 2.1. Emulsifiable concentrates | (a) | (b) | (c) | (d) |
|---|---|---|---|---|
| compound according to Preparatory Example 1 | 10% | 25% | 40% | 50% |
| calcium dodecylbenzenesulfonate | — | 5% | 8% | 6% |
| castor oil polyethylene glycol ether (36 moles of ethylene oxide) | — | 5% | — | — |
| tributylphenol polyethylene glycol ether (30 moles of ethylene oxide) | — | — | 12% | 4% |
| castor oil thioxilate | 25% | — | — | — |
| cyclohexanone | — | — | 15% | 20% |
| butanol | 15% | — | — | — |
| xylene mixture | — | 65% | 25% | 20% |
| ethyl acetate | 50% | — | — | — |

Emulsions of any required concentration can be produced from such concentrates by dilution with water.

| 2.2 Solutions | (a) | (b) |
|---|---|---|
| compound according to preparatory Example 1 | 10% | 5% |
| ethylene glycol monomethyl ether | — | — |
| polyethylene glycol (mol. wt. 400) | 70% | — |
| N—methyl-2-pyrrolidone | 20% | — |
| expoxidised coconut oil | — | 1% |
| ligroin (boiling range 160–190°) | — | 94% |

These solutions are suitable for application in the form of microdrops.

| 2.3. Granulates | (a) | (b) |
|---|---|---|
| compound according to Preparatory Example 1 | 5% | 10% |
| kaolin | 94% | — |
| highly dispersed silicic acid | 1% | — |
| attapulgite | — | 90% |

The active ingredient is dissolved in methylene chloride, the solution is sprayed onto the carrier, and the solvent is subsequently evaporated off in vacuo.

| 2.4. Dusts | (a) | (b) | (c) | (d) |
|---|---|---|---|---|
| compound according to Preparatory Example 1 | 2% | 5% | 5% | 8% |
| highly dispersed silicic acid | 1% | 5% | — | — |
| talcum | 97% | — | 95% | — |
| kaolin | — | 90% | — | 92% |

Ready for use dusts are obtained by intimately mixing the carriers with the active ingredient.

| 2.5. Wettable powders | (a) | (b) | (c) |
|---|---|---|---|
| compound according to Preparatory Example 1 | 25% | 50% | 75% |
| sodium lignosulfonate | 5% | 5% | — |
| sodium laurylsulfate | 3% | — | 5% |
| sodium diisobutylnaphthalenesulfonate | — | 6% | 10% |
| octylphenol polyethylene glycol ether (7–8 moles of ethylene oxide) | — | 2% | — |
| highly dispersed silicic acid | 5% | 10% | 10% |
| kaolin | 62% | 27% | — |

The active ingredient is thoroughly mixed with the adjuvants and the mixture is thoroughly ground in a suitable mill, affording wettable powders which can be diluted with water to give suspensions of the desired concentration.

| 2.6. Extruder granulate | |
|---|---|
| compound according to Preparatory Example 1 | 10% |
| sodium lignosulfonate | 2% |
| carboxymethylcellulose | 1% |
| kaolin | 87% |

The active ingredient is mixed and ground with the adjuvants, and the mixture is subsequently moistened with water. The mixture is extruded and then dried in a stream of air.

| 2.7. Coated granulate | |
|---|---|
| compound according to Preparatory Example 1 | 3% |
| polyethylene glycol (mol. wt. 200) | 3% |
| kaolin | 94% |

The finely ground active ingredient is uniformly applied, in a mixer, to the kaolin moistened with polyethylene glycol. Non-dusty coated granulates are obtained in this manner.

| 2.8. Suspension concentrate | |
|---|---|
| compound according to Preparatory Example 1 | 40% |
| ethylene glycol | 10% |
| nonylphenol polyethylene glycol ether (15 moles of ethylene oxide) | 6% |
| sodium lignosulfonate | 10% |
| carboxymethylcellulose | 1% |
| 37% aqueous formaldehyde solution | 0.2% |
| silicone oil in the form of a 75% aqueous emulsion | 0.8% |
| water | 32% |

The finely ground active ingredient is intimately mixed with the adjuvants, giving a suspension concentrate from which suspensions of any desired concentration can be obtained by dilution with water.

EXAMPLE 3

Biological Examples for Compounds According to Preparatory Example 1

3.1. Insecticidal stomach poison action: *Spodoptera littoralis*

Cotton plants are sprayed with a solution containing 400 ppm of the test compound.

After the spray coating has dried, the plants are populated with larvae of *Spodoptera littoralis* in the $L_1$ stage. Two plants are used per test compound. Evaluation of the mortality rate is made after 2, 4, 24, 48 and 72 hours. The test is carried out at 28° C. and 60% relative humidity. In this test, compounds according to Example 1 are 80 to 100% effective against *Spodoptera littoralis* larvae.

3.2. Action against *Lucilia sericata*

1 ml of an aqueous formulation containing 0.1% of test compound is added at 50° C. to 9 ml of a culture medium. Then about 30 freshly hatched *Lucilia sericata* larvae are added to the culture medium, and the insecticidal action is determined after 48 and 96 hours by evaluating the mortality rate. In this test, compounds according to Example 1 are 80 to 100% effective against *Lucilia sericata*.

3.3. Action against *Aedes aegypti*

A concentration of 12.5 ppm is obtained by pipetting a specific amount of a 0.1% solution of the test compound in acetone onto the surface of 150 ml of water in a beaker. After the acetone has evaporated, 30 to 40 two-day-old larvae of *Aedes aegypti* are put into the beaker containing the test compound. Mortality counts are made after 2 and 7 days.

Compounds according to Example 1 effect 100% mortality in this test.

3.4. Ovicidal action against *Heliothis virescens*

Corresponding amounts of a wettable powder formulation containing 25% by weight of the test compound are mixed with sufficient water to produce aqueous emulsions with active ingredient concentrations of 400 to 12.5 ppm. One day-old egg deposits of Heliothis on cellophane ® are immersed in these emulsions for 3 minutes and then collected by suction on round filters. The treated deposits are placed in petri dishes and kept in the dark. The hatching rate in comparison with untreated controls is determined after 6 to 8 days. Evaluation is made to determine the minimum concentration of compound required to effect 100% kill of the eggs.

In the above test, compounds according to Example 1 effect 100% mortality at 12.5 ppm.

3.5. Insecticidal contact action against *Myzus persicae*

Pea plants which have been reared in water to a height of about 4 cm are each populated with about 200 individuals of the species *Myzus persicae* before the start of the test. The treated plants are then sprayed to drip point with an aqueous suspension containing 400 ppm of the test compound. Two plants are used for each compound at its given concentration. A mortality count is made 48 hours after application. The test is carried out at 20°-22° C. and 60% relative humidity.

In this test, compounds according to Example 1 are 80 to 100% effective.

3.6. Action against soil insects (*Diabrotical balteata*)

5 maize seedlings about 1 to 3 cm in length and a disc of filter paper are immersed in an aqueous formulation containing 0.2 to 12.5 ppm of the test compound. The moist filter paper disc is placed at the bottom of a 200 ml plastic beaker, and then the 5 treated maize seedlings together with 10 larvae of diabrotica balteata in the second to third larval stage are placed in the beaker. Two tests are carried out for each test compound at its given concentration. The beakers containing the larvae are kept for 6 days at daylight, a relative humidity of 40 to 60% and at temperature of 22° to 24° C. The percentage kill of the test insects is then determined.

In this test, compounds according to Example 1 are 100% effective at a concentration of 12.5 ppm.

3.7. Action against *Laspeyresia pomonella* (eggs):

Egg deposits of *Laspeyrasia pomonella* not more than 24 hours old are immersed on filter paper for 1 minute in an aqueous acetonic solution containing 400 ppm of the test compound.

After the solution has dried, the eggs are placed in petri dishes and kept at a temperature of 28° C. The percentage of larvae hatched from the treated eggs is evaluated after 6 days.

Compounds according to Example 1 are 100% effective in this test.

What is claimed is:

1. A method of controlling pests of animals and plants selected from insects, representatives of the order Acarina and phytopathogenic fungi, which method comprises applying to said animals or plants a pesticidal composition comprising a pesticidally effective amount of compound of formula I

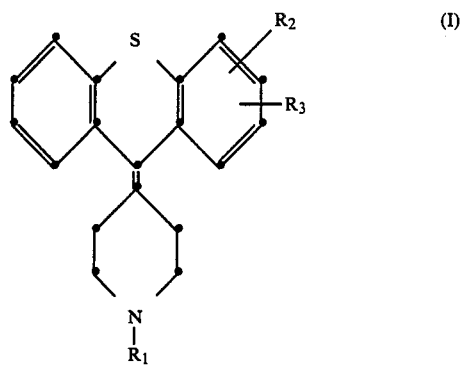

wherein
$R_1$ is hydrogen, $C_1$-$C_4$alkyl, $C_3$-$C_5$alkenyl, $C_3$-$C_5$alkynyl, cyano or —$COR_4$,
$R_2$ and $R_3$ independently of each other are hydrogen, halogen, $C_1$-$C_4$alkyl, $C_1$-$C_4$alkoxy, $C_1$-$C_4$haloalkyl or nitro,
$R_4$ is

$C_1$-$C_4$alkyl, $C_1$-$C_4$alkoxy-$C_1$-$C_4$alkyl, $C_1$-$C_4$haloalkyl, $C_3$-$C_6$cycloalkyl,

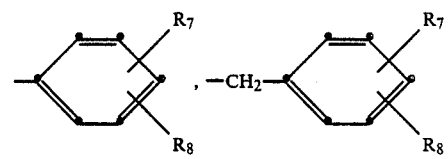

or $C_1-C_4$alkoxycarbonyl, $R_5$ and $R_6$ independently of each other are hydrogen, $C_1-C_4$alkyl or $C_1-C_4$alkoxy and $R_7$ and $R_8$ independently of each other are hydrogen, halogen, $C_1-C_4$alkyl, $C_1-C_4$alkoxy or nitro, or a salt thereof, and a pesticidally acceptable carrier.

2. A pesticidal method according to claim 1, which comprises a active ingredient a compound of formula Ia

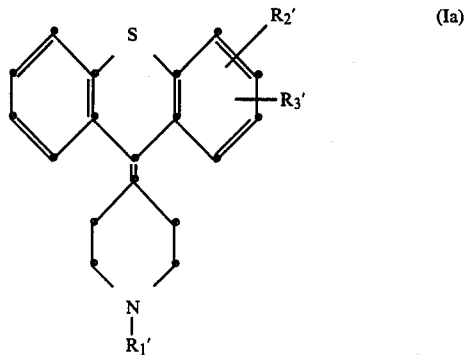

wherein $R_1'$ is hydrogen, $R_2'$ is bromine, $C_2-C_4$alkyl, $C_2-C_4$alkoxy, —$CHF_2$ or nitro and $R_3'$ is hydrogen, halogen, $C_1-C_4$alkyl, $C_1-C_4$alkoxy, $C_1-C_4$haloalkyl or nitro or $R_1'$ is ethyl, propyl, isopropyl, n-butyl, isobutyl, sec-butyl or tert-butyl and $R_2'$ and $R_3'$ independently of each other are hydrogen, fluorine, bromine, $C_1-C_4$alkyl, $C_1-C_4$alkoxy, —$CHF_2$ or nitro or $R_1'$ is propyl or isopropyl, $R_2'$ is chlorine and $R_3'$ is hydrogen, halogen, $C_1-C_4$alkyl, $C_1-C_4$alkoxy, $C_1-C_4$haloalkyl or nitro or $R_1'$ is cyano and $R_2'$ and $R_3'$ are hydrogen or $R_1'$ is —$COR_4'$ or —$CH_2$—$C \equiv CH$, $R_2'$ is $R_3'$ independently of each other are hydrogen, halogen, $C_1-C_4$alkyl, $C_1-C_4$alkoxy, $C_1-C_4$haloalkyl or nitro, $R_4'$ is

$C_1-C_4$alkyl, $C_1-C_4$haloalkyl, $C_3-C_6$cycloalkyl,

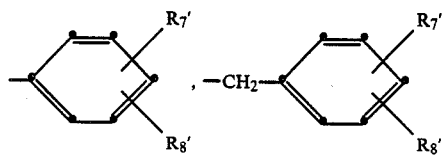

or carbonyloxy-$C_1-C_4$alkyl, $R_5'$ and $R_6'$ independently of each other are hydrogen, $C_1-C_4$alkyl or $C_1-C_4$alkoxy and $R_7'$ and $R_8'$ independently of each other are hydrogen, halogen, $C_1-C_4$alkyl, $C_1-C_4$alkoxy or nitro or $R_1'$ is —$CH_2$—$CH=CH_2$ and $R_2'$ and $R_3'$ independently of each other are hydrogen, halogen, $C_1-C_4$alkyl, $C_1-C_4$alkoxy or nitro, or a salt thereof.

3. The pesticidal method according to claim 2 which comprises as active ingredient

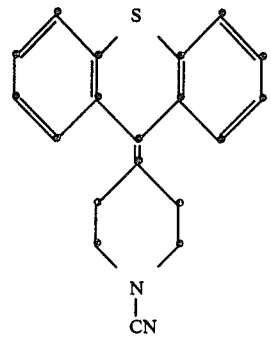

4. The pesticidal method according to claim 2 which comprises as active ingredient

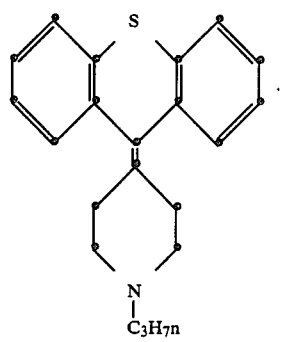

5. The pesticidal method according to claim 2 which comprises as active ingredient

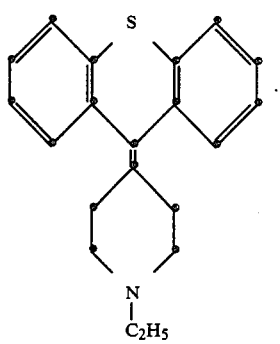

6. The pesticidal method according to claim 2 which comprises as active ingredient

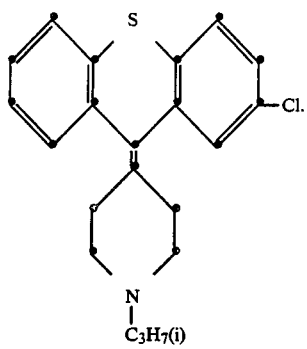

7. The pesticidal method according to claim 2 which comprises as active ingredient

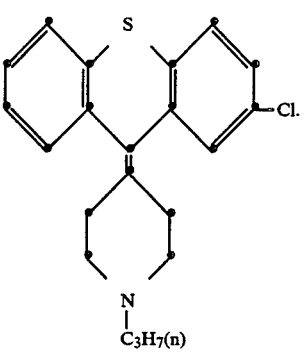

8. The pesticidal method according to claim 2 which comprises as active ingredient

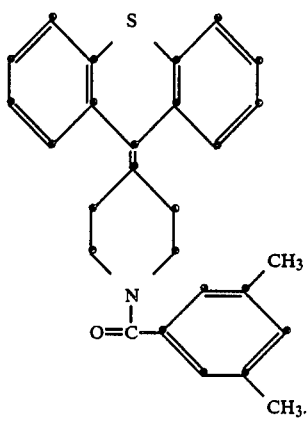

9. The pesticidal method according to claim 2 which comprises as active ingredient

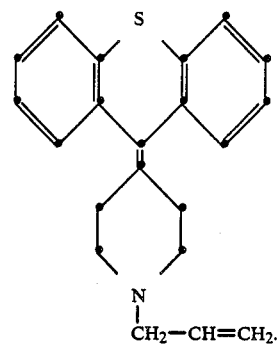

10. The pesticidal method according to claim 2 which comprises as active ingredient

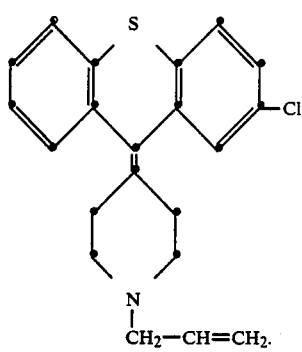

11. The pesticidal method according to claim 2 which comprises as active ingredient

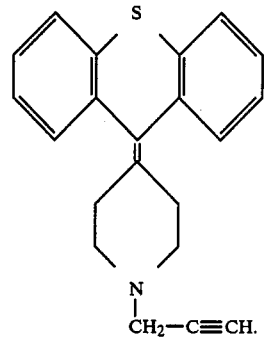

12. The pesticidal method according to claim 2 which comprises as active ingredient

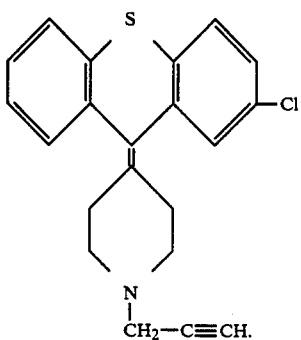

13. The pesticidal method according to claim 2 which comprises as active ingredient

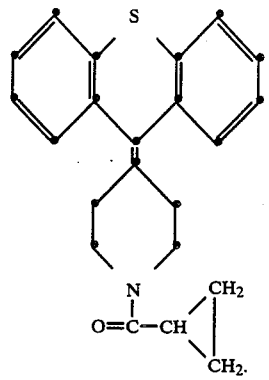

14. The pesticidal method according to claim 2 which comprises as active ingredient

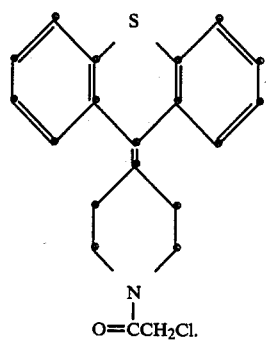

15. The pesticidal method according to claim 2 which comprises as active ingredient

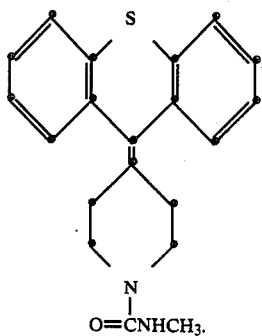

16. The pesticidal method according to claim 2 which comprises as active ingredient

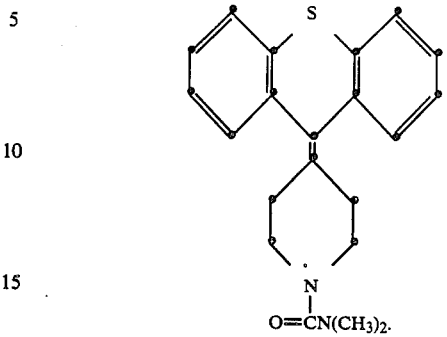

17. The pesticidal method according to claim 2 which comprises as active ingredient

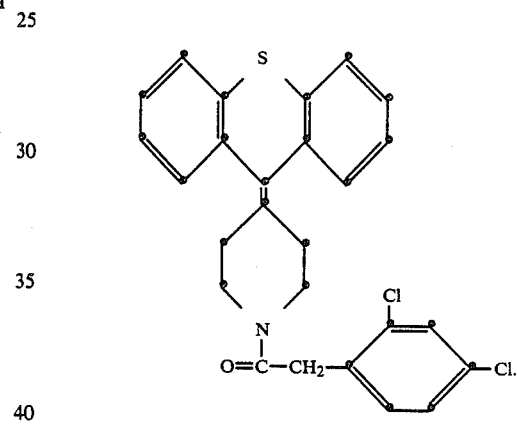

18. The pesticidal method according to claim 2 which comprises as active ingredient

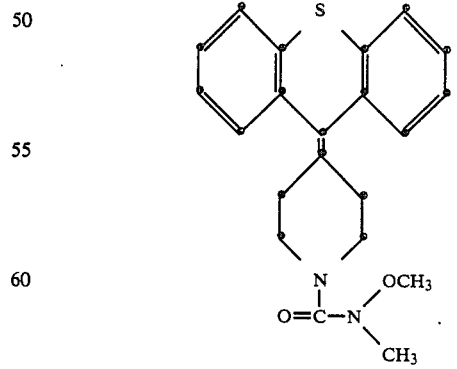

19. The pesticidal method according to claim 2 which comprises as active ingredient

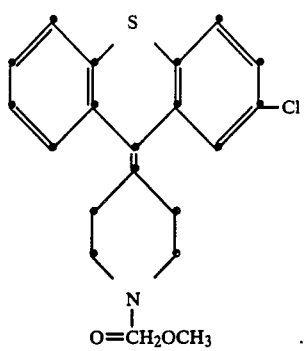

20. The pesticidal method according to claim 2 which comprises as active ingredient

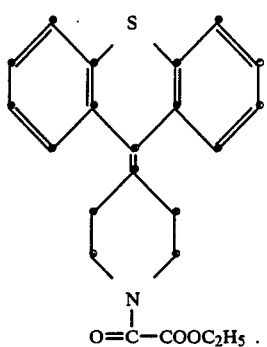

21. The pesticidal method according to claim 2 which comprises as active ingredient

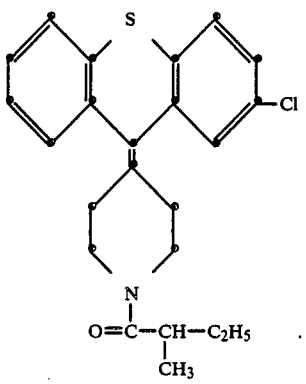

22. The pesticidal method according to claim 2 which comprises as active ingredient

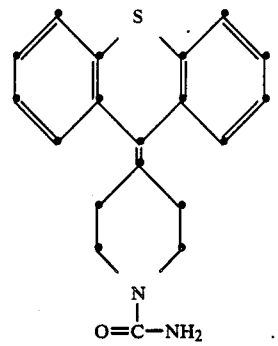

23. The pesticidal method according to claim 2 which comprises as active ingredient

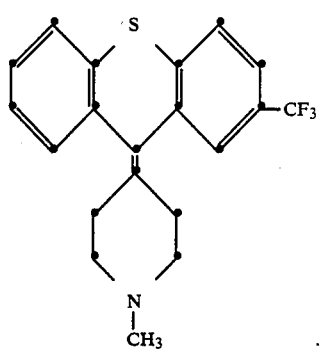

24. The pesticidal method according to claim 2 which comprises as active ingredient

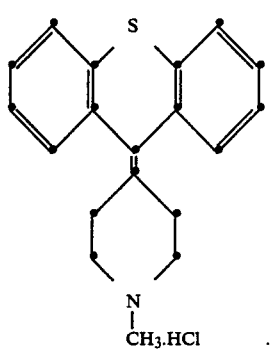

25. The pesticidal method according to claim 2 which comprises as active ingredient

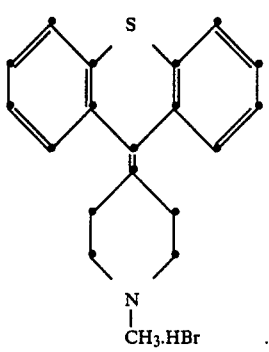

26. The pesticidal method according to claim 2 which comprises as active ingredient
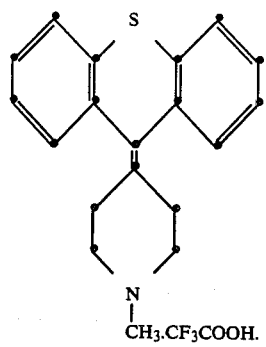
CH₃.CF₃COOH.
27. The pesticidal method of claim 2 which comprises as active ingredient
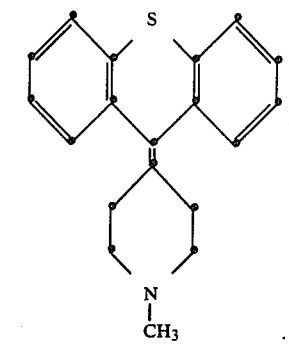
28. A method according to claim 1 for controlling insects and representatives of the order Acarina.
29. A method according to claim 1 for controlling phytopathogenic fungi.
* * * * *